United States Patent [19]

Müller et al.

[11] 4,292,158
[45] Sep. 29, 1981

[54] OXYGEN SENSOR OF THE POLAROGRAPHIC TYPE, PARTICULARLY FOR USE WITH INTERNAL COMBUSTION ENGINES

[75] Inventors: Klaus Müller, Tamm; Helmut Maurer, Schwieberdingen; Hermann Dietz, Gerlingen; Karl-Hermann Friese; Wolfgang Leibfried, both of Leonberg; Günther Stecher, Ludwigsburg; Ernst Linder, Mühlacker, all of Fed. Rep. of Germany

[73] Assignee: Robert Bosch GmbH, Stuttgart, Fed. Rep. of Germany

[21] Appl. No.: 157,303

[22] Filed: Jun. 9, 1980

[30] Foreign Application Priority Data

Jun. 9, 1979 [DE] Fed. Rep. of Germany ....... 2923483

[51] Int. Cl.³ ............................................ G01N 27/58
[52] U.S. Cl. ................................................ 204/195 S
[58] Field of Search ............................ 204/195 S, 1 S

[56] References Cited

FOREIGN PATENT DOCUMENTS 1523550  9/1978  United Kingdom ............ 204/195 S

Primary Examiner—G. L. Kaplan
Attorney, Agent, or Firm—Frishauf, Holtz, Goodman & Woodward

[57] ABSTRACT

To simplify manufacture and provide a polarographic sensor of high response speed, operating according to the current limiting principle, an oxygen molecule migration barrier is provided leading to the cathode by separating the cathode from the space where the gas to be tested exists by a wall through which a hole is provided which extends therethrough to a small space immediately above the cathode defined by support elements placed immediately on the cathode. The hole, or a plurality of holes, is so dimensioned that the diameter thereof, with respect to its length, is small, with diameters of between 0.01 to 0.06 mm and a length of at least about 1 mm being suitable.

18 Claims, 7 Drawing Figures

OXYGEN SENSOR OF THE POLAROGRAPHIC TYPE, PARTICULARLY FOR USE WITH INTERNAL COMBUSTION ENGINES

The present invention relates to an oxygen sensor to determine the oxygen content of gases, especially of the gases resulting from a combustion process, and particularly of the exhaust gases of internal combustion engines, for example of the automotive type, and operating according to the polarographic principle.

BACKGROUND AND PRIOR ART

Various types of oxygen sensors have been proposed; polarographic oxygen sensors operate in accordance with the well known principle that, if an ion conductor forming a solid electrolyte body has electrodes applied thereto across which a voltage is placed, the current in the so-formed circuit will be representative of the oxygen concentration in the gases to which the element is exposed. Reference is made, for example, to U.S. Pat. No. 3,691,023, Ruka, and to U.S. application Ser. No. 637,998, filed May 12, 1975, and now abandoned (and published as British Pat. No. 1,523,550, Canadian Pat. No. 1,071,709, German Disclosure Document No. 26 54 483). The sensor of the aforementioned application Ser. No. 637,998 has a space in which the cathode electrode is placed which is separated from the gas to be sensed, and which is in communication with the gas to be sensed by an opening. By varying the size of the opening, diffusion of gas can be matched to the size of the electrode. If the opening is too large, the current which is measured in the circuit is practically independent of the actual concentration level of oxygen within the test gas, since the sensor will no longer operate in the diffusion limit current range. The space in which the cathode is placed is comparatively large, so that the effect will be that of exposing the cathode electrode to a surface of mixing chamber in which mixing is carried out slowly and with substantial inertia so that the response speed of sensor to changes in the oxygen level is slow. Such sensors, as described, are comparatively large and of complex manufacture.

THE INVENTION

It is an object to provide a sensor which has high response speed and, preferably, also is simple and easy to make.

Briefly, the cathode has support posts, ridges or bars secured thereto which support a wall of a gas-impervious substance through which an opening is provided, the opening forming an oxygen molecule migration path while presenting a diffusion barrier; the support posts, ridges or the like and the opposite wall define a system of spaces immediately adjacent the cathode. The hole forms an elongated opening of a length which is long with respect to its diameter or maximum cross-sectional dimension to form communicating openings with the gas, the oxygen concentration of which is to be measured. Screen printing technology can be used to manufacture the sensor.

The sensor has the advantage that the spaces immediately adjacent the cathode are extremely small and that, therefore, any change in concentration of oxygen content is reflected in output due to the opening which is long with respect to its cross section. The "dead space" adjacent the electrode is a minimum. The sensor can be made by readily available manufacturing steps, in compact form.

DRAWINGS

FIGS. 5 and 6 show improvements of the example illustrated in FIG. 3.

Figure 1:
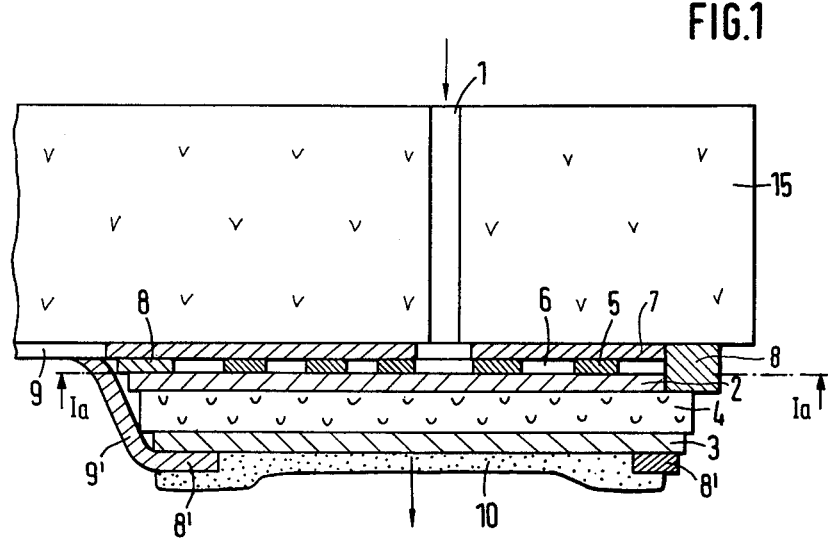
FIG. 1 is a cross-sectional view through an embodiment of the sensor, in which the sensing plate is secured to an electrically neutral ceramic plate or disk.
Figure 1A:
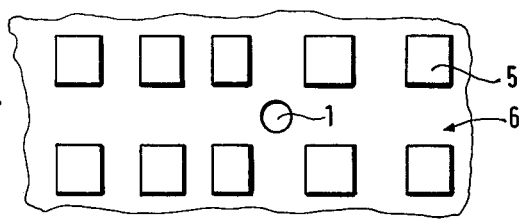
FIG. 1a is a fragmentary view along lines Ia—Ia of FIG. 1.

Embodiment of FIG. 1: A carrier plate 15 with its relevant region of about 4×5 mm size, and a thickness of 1.2 mm, is provided, made of a dense ceramic material, for example aluminum oxide. In accordance with a feature of the invention, carrier plate 15 is formed with a through-opening 1 of about 0.05 mm diameter. Instead of a single hole 1—which, for example, is of circular cross section—it is possible to apply a plurality of openings, each of a diameter of about 0.01 to 0.02 mm. Such smaller openings should be located on the plate 15 in such a manner that about one opening per square millimeter is provided. Alternatively, the carrier plate 15 could be a ceramic of coarse-pore characteristic, with a glaze thereover which is gas-tight, and in which the holes are formed to extend through the glaze, typically a glass cover. The sensor has a cathode 2 and an anode 3, and an electrolyte body 4 located between cathode 2 and anode 3. Electrodes 2, 3 either are made of platinum, or a mixture of platinum and stabilized zirconium dioxide, for example about 40% (by volume) of zirconium dioxide. Electrolyte body 4, as well known, is made of stabilized zirconium dioxide.

In accordance with a feature of the invention, support elements 5, for example of about square cross section and, preferably, positioned in a rectangular grid pattern, are located between the cathode 2 and the support carrier 15, to define gas distribution or dispersion spaces 6 between the support elements 5 and the surface of plate 15 facing the cathode 2. The support elements 5 preferably are made of the same material as the cathode 2, so that the exposed outer surfaces of the support elements 5 provide an additional electrode surface. The spaces 6 are in communication with the hole 1, so that oxygen molecules can reach the cathode 2 via the spaces 6.

It is desirable to arrange a layer of platinum 7 between the support elements 5 and the carrier plate 15 in order to uniformly supply the cathode 2 with electrons. Arranging, further, a frame 8 at the circumference of the cathode the layer 7 and the electrolyte 4 inhibits an oxygen bypass to the cathode. A similar frame 8' of platinum can be applied to the anode 3 to improve the electron supply. The frame 8' and the layer 7 terminate in conductive paths 9, 9', respectively, which are connected to suitable terminals on the support 15 for subsequent connection to a voltage source, for example to a battery of about 1 V operating voltage. The anode 3, at the side opposite the body 4, has a porous ceramic protective layer 10 applied thereto, for example a porous aluminum oxide, through which oxygen which is formed at the anode, can escape.

The gas to be measured is in communication with the upper side—with respect to FIG. 1—of the carrier plate 15. Gas passes through the hole 1 into the spaces 6 and at that point to the cathode. The hole 1 has an end portion, or extends throughout its entire length in a direction perpendicular to the plane of space 6, which is also that of cathode 2. Thus, gas is conducted to the cathode 2 transversely to the main direction of the sensor. Due to the voltage applied between the cathode and anode at the conductors 9, 9', respectively, the oxygen is reduced at the three-phase boundary of cathode-electrolyte-gas, and will pass in the form of oxygen ions through the electrolyte 4 to the anode 3, where the oxygen ions are oxidized to oxygen molecules, which can escape through the porous layer 10. The oxygen ions migrating between cathode and anode through the electrolyte body 4 cause current flow between the cathode and the anode, the magnitude of which depends on the number of oxygen molecules reaching the cathode, when the sensor operates within the range of the diffusion limit current.

Figure 2:
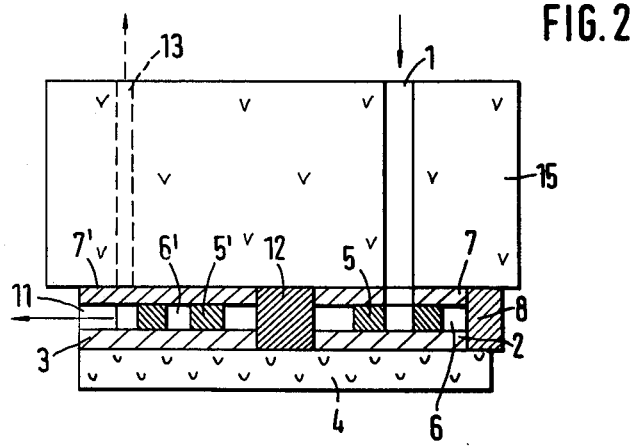
FIG. 2 illustrates another embodiment of a sensor in which the sensor plate is secured to an electrically neutral disk.

The embodiment of FIG. 1 illustrates a sensor based on a bilateral construction, that is, cathode 2 and anode 3 are placed at opposte sides of the electrode body 4. FIG. 2 illustrates a unilateral arrangement, in which the cathode 2 and the anode 3 are located on the same side of the electrode body 4.

Embodiment of FIG. 2: A separating wall 12 made of a dense, non-conductive ceramic such as aluminum oxide, separates the gas space of the cathode 2—the right half of the sensor in FIG. 2—from the gas space of the anode 3 which forms the left half, as seen in FIG. 2. As in the example of FIG. 1, oxygen is passed through the hole 1 in the carrier plate 15 in the spaces 6 defined by the support plates 5, and thus comes in contact with the cathode 2. The oxygen ions formed at the cathode 2 migrate through the electrolyte 4 to the anode 3 where they are oxidized again to form molecular oxygen, which will reach the spaces 6' over the anode and can then escape either through a duct 11 or through an opening 13 which may be formed in the plate 15. The spaces 6', the support 5' and the hole 13 can all be similar to the spaces 5, 6 and the hole 1 at the right side of FIG. 2. The frame 8 seals the gas space at the cathode side towards the edge, so that gas can diffuse only through the opening 1. Again, as in the example of FIG. 1, it is desirable to place a platinum layer 7, 7' between the carrier plate 1 and the electrode carrier plate 15, the platinum layers 7, 7' being in contact with the respective support elements 5, 5'.

Figure 3:
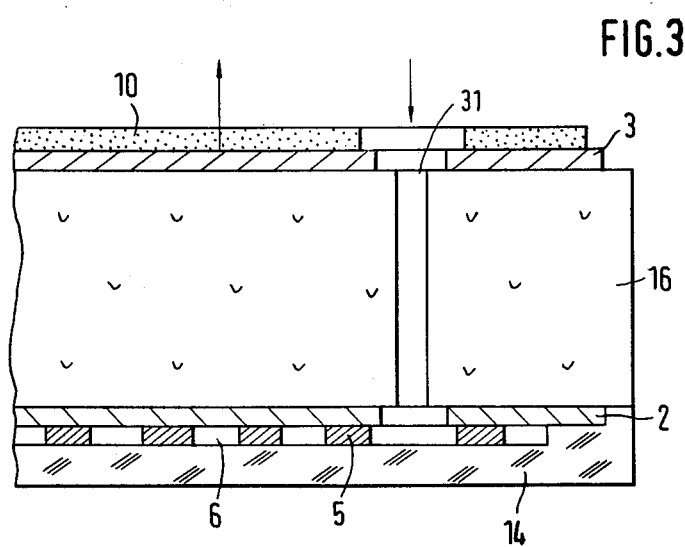
FIGS. 3 to 6 are cross-sectional views in which the carrier plate at the same time forms the electrolyte body, and in which, specifically.
Figure 4:
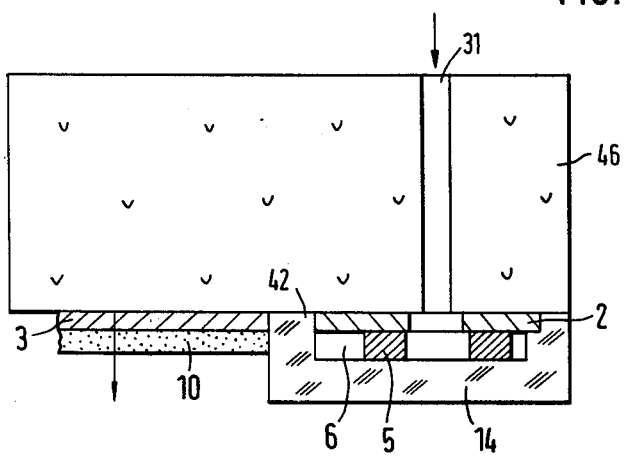

Embodiment of FIGS. 3 to 6: The carrier plate 16 is, simultaneously, the electrolyte body, so that the separation between a support carrier and the solid electrolyte body need not be made. The arrangement of FIG. 3 is bilateral—corresponding somewhat to FIG. 1; the arrangement of FIG. 4 is unilateral, corresponding somewhat to FIG. 2.

Embodiment of FIG. 3: The cathode 2 is shown at the lower side of FIG. 3, the anode 3 at the top side (reversed with respect to FIG. 1). Oxygen reaches the cathode from the anode side, that is, from the top—as in FIG. 1—through the hole 31. Hole 31 extends not only through the solid electrolyte body 16—for example of zirconium dioxide—but also through the anode 3 and the cathode 2. Oxygen is distributed in the spaces 6 and comes, thereby, in contact with the cathode 2. The spaces 6 between the cathode 2 and the opposte wall of a cover 14 are formed by support elements 5 which, as before, can be formed of the electrode materials themselves. The cover 14 is a gas-tight cover which, for example, may be of glass. An intermediate platinum layer can be applied between the cover 14 and the supports 5, similar to the layer 7 of FIG. 1, in order to insure good electron supply. Platinum frames similar to frames 8, 8' (FIG. 1) can be used—not shown in FIG. 3. It is desirable to cover the anode 3 by a porus protective ceramic layer 10. Ceramic layer 10 should be sufficiently porous to permit ready escape of oxygen molecules therethrough.

Embodiment of FIG. 4: A unilateral sensor element in which the carrier 46, of zirconium dioxide, functions simultaneously as the carrier and the solid electrolyte body. Cathode 2 and anode 3 are located at the same side of the electrolyte 46 and are separated from each other by a gas-tight separating wall 42. The separating wall 42, preferably, forms a portion of, and is integral with, the gas-tight cover 14 which, together with the support elements 5, defines the space 6.

In operation, oxygen molecules migrate through the hole 31 in the electrolyte 16 and disperse in the spaces 6 to reach the cathode 2. The oxygen molecules are reduced at the three-phase boundary gas/cathode 2/electrolyte 46 and, in the form of oxygen ions, reach the anode 3 through the solid electrolyte body 46, to be re-oxidized to molecular oxygen thereat, for escape through the porous protective layer 10.

The advantage of the system in accordance with FIG. 4 is this: Mixing of oxygen which passes through the hole 1 to the cathode 2 with escaping oxygen is prevented, since introduction of the oxygen to the cell occurs at one lateral side thereof, whereas emission of oxygen from the cell occurs at the other side. A similar effect can be obtained in accordance with the arrangement of FIG. 3 if care is taken to separate oxygen being admitted and released by mechanical means, as illustrated specifically in FIGS. 5 and 6.

Figure 5:
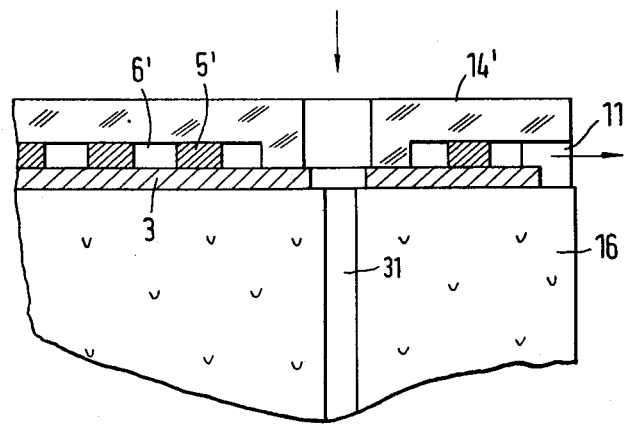

Embodiment of FIG. 5: This arrangement is suitable for use with the embodiment of FIG. 3. Support elements 5', similar to those of FIG. 2, are formed on the anode 3. A gas-tight cover 14' is placed over the support elements 5', leaving open sufficient space for the hole 31 to pass therethrough. Oxygen emitted from the anode 3 can escape through a lateral duct 11.

Figure 6:
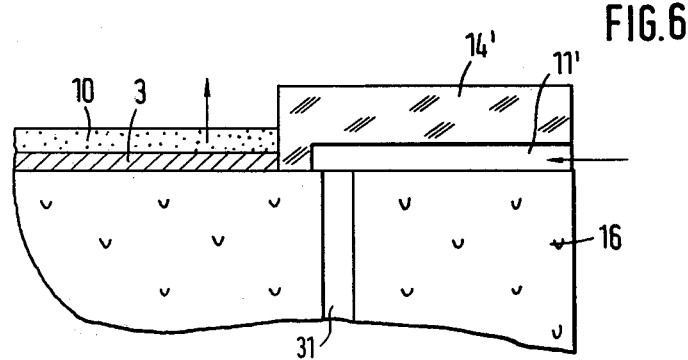

The arrangement according to FIG. 6 also can be used with the embodiment of FIG. 3 by arranging the gas-tight cover in such a manner that the oxygen being conducted to the cathode 2 is separately guided. The gas-tight cover 14' is formed with an elongated duct 11' which extends at the upper edge of the electrolyte 16 over to the hole 31. The anode is removed at the region where the cover plate 14' or the portion 14' and the duct 11' are located.

Common to all the embodiments is the formation of support elements 5, 5' which, preferably, have approximately rectangular block shape or, at least, approximately square or round cross section of a height of between 0.01 to 0.05 mm. The spaces can also be formed by interrupted ridges built up or formed on the respective electrode, the width of the spaces 6 being between about 0.2 to 0.5 mm. The hole 1, 31 leading to the spaces 6 has a diameter which is small with respect to its length; a typical diameter is between 0.01 to 0.06 mm, whereas the length of the hole, that is, the thickness of the materials through which it extends, is more than 1 mm. The supports 5, 5' can be arranged in any suitable manner, but preferably are placed in form of a grid pattern, and approximately 0.4 mm square.

Various changes and modifications may be made, and features described in connection with any one of the embodiments may be used with any of the others, within the scope of the inventive concept.

The spaces 6 can be formed in various ways; two methods to make such small spaces, bounded by metallic layers which form electrodes, are described and claimed in U.S. application Ser. No. 145,738, filed May 1, 1980, "Flat Electrochemical Sensor and Method of its Manufacture" assigned to the assignee of the present application, and having common co-inventors Maurer, Müller, Linder and Stecher, together with others,

We claim:

1. Polarographic sensor to determine the oxygen content of gases, particularly combustion gases, especially when emanating from an internal combustion engine, and operating in accordance with diffusion limiting current principle having a solid electrolyte body (4, 16, 46);

an anode electrode (3) applied to a surface portion of said body;

a cathode electrode (2) applied to another surface portion of said body;

means (9, 9') adapted to apply a voltage across said electrodes;

means (15, 16, 46) forming a wall separating the cathode from an ambient space in which the gas, the oxygen of which is to be determined, occurs, and an opening formed in said wall to conduct oxygen molecules to the cathode, comprising, in accordance with the invention, support elements (5) located between the cathode and said wall and defining, therebetween, a system of intermediate distribution or dispersion spaces (6);

and wherein the opening in said wall comprises at least one hole (1,31) which has a length which is long in relation to the diameter of the hole and is in gas communication with said distribution or dispersion spaces.

2. Sensor according to claim 1, wherein the support elements (5), in plan view, are approximately square.

3. Sensor according to claim 1, wherein the hole, or holes, has a diameter of between 0.01 to 0.06 mm, and a length of at least 1 mm;

and wherein the spaces (6) have a height of between 0.01 and 0.05 mm, and a width, between the support elements, of between 0.2 to 0.5 mm.

4. Sensor according to claim 1, wherein a plurality of holes (1, 31) are provided, spaced from each other by at least 1 mm, and distributed over the surface of said wall in an approximate grid pattern, the diameter of said holes being in the order of about 0.01 to 0.02 mm and have a length of more than 1 mm;

and wherein the height of the spaces (6) is approximately of the same order of magnitude as the diameter of the holes, the spaces between the support elements (5) being about 10 to 50 times the height of the spaces (6).

5. Sensor according to claim 1, wherein the support elements (5) comprise electron conductive material.

6. Sensor according to claim 5, wherein the support elements are made of the same material as that of the electrode with which they are in contact.

7. Sensor according to claim 1, wherein the electrodes (2, 3) comprise at least one of the materials selected from the group consisting of platinum and platinum-zirconium dioxide mixture.

8. Sensor according to claim 7, wherein the support elements (5) comprise the same material as that of the electrodes.

9. Sensor according to claim 1, further comprising a platinum coating (7) located at the surface of the wall facing the cathode, in engagement with said support elements, and electrically conductively connected to the cathode.

10. Sensor according to claim 9, further including a frame (8) laterally surrounding the cathode (2), made of a non electrode material.

11. Sensor according to claim 1, further includes a frame (8) laterally surrounding the cathode (2), made of a non electrode material.

12. Sensor according to claim 1, wherein the means defining said wall and the solid electrolyte body comprise the same element 16, 46 and said hole (31) extends through the solid electrolyte body.

13. Sensor according to claim 12, further comprising gas-impervious cover means (14') formed with a hole therethrough and positioned over said solid electrolyte body, the hole through said cover means matching the hole through the solid electrolyte body.

14. Sensor according to claim 13, further comprising a connecting duct (11') leading through said cover means to said hole (31).

15. Sensor according to claim 1, further comprising anode spacing support elements (5') positioned over the anode (3);

means (3, 14') covering the anode support elements (5') at the side remote from the anode (3) to define anode spaces;

and duct means (11) providing communication between said anode spaces and the ambient space surrounding the sensor.

16. Sensor according to claim 1, wherein the means defining said wall comprises a carrier or support plate (15) of ceramic material.

17. Sensor according to claim 1, wherein said at least one hole (1, 31) has a terminal portion extending in a plane essentially transverse to the surface portion on which the cathode electrode is applied.

18. Sensor according to claim 1, wherein said at least one hole (1, 31) extends at essentially a right angle with respect to the surface portion of said body to which said cathode electrode (2) is applied.

* * * * *